United States Patent [19]

Cale, Jr.

[11] 4,226,861
[45] Oct. 7, 1980

[54] N-LOWER-ALKYL 3-PHENOXY-1-AZETIDINECARBOXA-MIDES

[75] Inventor: Albert D. Cale, Jr., Mechanicsville, Va.

[73] Assignee: A. H. Robins Company, Inc., Richmond, Va.

[21] Appl. No.: 29,800

[22] Filed: Apr. 13, 1979

Related U.S. Application Data

[63] Continuation-in-part of Ser. No. 897,462, Apr. 18, 1978, abandoned.

[51] Int. Cl.² .................. C07D 205/04; C07D 31/395
[52] U.S. Cl. .................. 424/244; 260/239 A
[58] Field of Search .................. 260/239 A, 239 R; 424/244

[56] References Cited

U.S. PATENT DOCUMENTS 3,823,006  7/1974  Lorenz ........................... 260/239 A
4,031,221  6/1977  Helsley et al. ..................... 424/267

OTHER PUBLICATIONS

Testa et al., Res. Prog. Org.–Biol. & Medicinal Chem., vol. 1, pp. 557–558, (1964).

*Primary Examiner*—Mark L. Berch

[57] ABSTRACT

N-Lower-alkyl 3-phenoxy-1-azetidinecarboxamides having the formula:

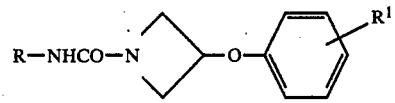

wherein R is alkyl and $R^1$ is hydrogen, aminocarbonyl and trifluoromethyl having central nervous system activity particularly anti-convulsant activity, are disclosed.

21 Claims, No Drawings

N-LOWER-ALKYL 3-PHENOXY-1-AZETIDINECARBOXAMIDES

This application is a continuation-in-part of copending application Ser. No. 897,462 filed Apr. 18, 1978 now abandoned.

BACKGROUND OF THE INVENTION

1. Field of the Invention

The present invention relates to certain novel heterocyclic compounds and more particularly to N-lower-alkyl 3-phenoxy-1-azetidinecarboxamides, compositions thereof and methods of making and using same.

2. Description of the Prior Art

N-Lower-alkyl 3-phenoxy-1-azatidinecarboxamides have not been described in the literature prior to the present invention.

SUMMARY OF THE INVENTION

The invention is especially concerned with novel N-lower alkyl 3-phenoxy-1-azetidinecarboxamides having the formula:

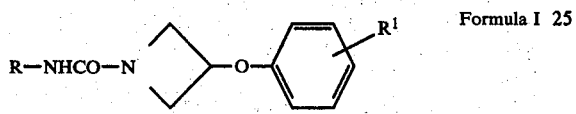

Formula I wherein;

R is lower alkyl, and $R^1$ is hydrogen, aminocarbonyl and trifluoromethyl.

The compounds of Formula I are useful because of their pharmacological action on the central nervous system. In particular, the novel compounds of Formula I possess anti-convulsant activity.

Anticonvulsant properties were determined using groups of five adult female mice. The mice were given 50 and 150 mg/kg, i.p., of a test drug 30 minutes prior to electrical or chemical challenge.

Animals were challenged electrically by placing brass electrodes on the corneas and applying an electrical stimulus (60 Hz, 5 msec. pulse width, 34 mA intensity) for 0.2 seconds by way of a Grass Stimulator and constant current unit and a Hunter Timer. The absence of tonic seizures upon cessation of the simuli was scored as protection in that animal. The number of animals protected from tonic seizures at each dose was determined.

For chemical challenge, each animal received a convulsant dose of pentylenetetrazole (120 mg/kg, i.p.). Complete suppression of tonic seizures or prevention of death of the animal during the next hour was scored as protection in that animal.

It is, therefore, an object of the present invention to provide certain novel N-lower-alkyl 3-phenoxy-1-azetidine-carboxamides, compositions thereof, and methods of making and using same. Another object is to provide novel N-lower-alkyl 3-phenoxy-1-azetidinecarboxamides having central nervous system activity. Other objects of the invention will be apparent to one skilled in the art and still other objects will become apparent hereinafter.

In the foregoing Formula I and where they appear elsewhere throughout this specification, the terms have the following significance.

The term "lower alkyl" as used herein includes alkyl radicals having one to six carbon atoms and includes such groups as methyl, ethyl, propyl, butyl, amyl and hexyl. Lower alkyl groups having one to four carbon atoms are preferred.

The term "phenoxy" as used includes the unsubstituted phenoxy group and the monosubstituted phenoxy group wherein the substituent is an aminocarbonyl or a trifluoromethyl group.

The compounds of the present invention may be conveniently prepared by contacting the appropriate 3-phenoxyazetidine of the formula:

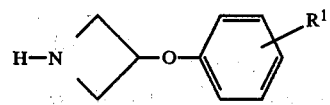

wherein $R^1$ is defined as hereinbefore with the appropriate isocyanate of the formula:

NCO wherein R is defined as hereinabove. The reaction is carried out in the presence of a dry aprotic solvent such as benzene, toluene or xylene. Benzene is a preferred solvent. The temperature of the reaction can vary from about 5° C. to about 20° C. and time can vary from about 30 minutes to about 24 hours.

The 3-phenoxyazetidines are novel compounds and are disclosed in copending application Ser. No. 886,487, filed Mar. 14, 1978.

The following examples describe in detail methods which have been devised for their preparation. It will be apparent to those skilled in the art that modifications may be practiced without departing from purpose and intent of the disclosure.

EXAMPLE 1

N-Methyl 3-phenoxy-1-azetidinecarboxamide

The methanesulfonate of 3-phenoxyazetidine (10.5 g., 0.043 mole) was partitioned between 50 ml of benzene and 25 ml. of dilute sodium hydroxide. The benzene layer was dried over calcium sulfate and filtered. The filtrate was treated with 2.6 g. (0.043 mole) of methylisocyanate and the solution was stirred at room temperature for 18 hours. The resulting mixture was concentrated at reduced pressure and the residue was crystallized from a mixture of ethyl acetate-isopropyl ether to give 1.2 g. (14%) of product (m.p. 139°–141° C.).

Analysis: Calculated for $C_{11}H_{14}N_2O_2$: C, 64.06; H, 6.84; N, 13.58. Found: C, 63.85; H, 6.81; N, 13.49.

EXAMPLE 2

N-Methyl 3-(2-aminocarbonylphenoxy)-1-azetidinecarboxamide

To 8.0 g. (0.028 mole) of 2-(3-azetidinyloxy)benzamide stirring in 100 ml of dry benzene was added dropwise 1.6 g. (0.028 mole) of methylisocyanate with ice bath cooling. Stirring was continued at room temperature for 24 hours. The solid material was filtered and was recrystallized from 95% ethanol. The product (4.0 g., 57%) melted at 236°–240° C.

Analysis: Calculated for $C_{12}H_{15}N_3O_3$: C, 57.82; H, 6.07; N, 16.86. Found: C, 57.74; H, 6.11; N, 16.48.

EXAMPLE 3

N-Methyl 3-(4-trifluoromethylphenoxy)-1-azetidinecarboxamide

The oxalic acid salt of 3-(4-trifluoromethylphenoxy) azetidine (13.0 g., 0.042 mole) was partitioned between 50 ml. of benzene and 50 ml. of potassium hydroxide solution. The benzene layer was dried over calcium sulfate and filtered, and to the stirring dried benzene solution was added 2.6 g. (0.046 mole) of methyl-isocyanate. Stirring was continued overnight. The mixture was concentrated at reduced pressure and the solid residue was recrystallized from a mixture of isopropyl ether-ethyl acetate. The product weighed 7.5 g. (65%) and melted at 154°-157° C.

Analysis: Calculated for $C_{12}H_{13}F_3N_2O_2$: C, 52.56; H, 4.78; N, 10.21. Found: C, 52.62; H, 4.75; N, 10.17.

EXAMPLE 4

N-Methyl 3-(3-trifluoromethylphenoxy)-1-azetidinecarboxamide

To 6.0 g. (0.024 mole) of 3-(3-trifluoromethylphenoxy) azetidine in 50 ml. of dry benzene was added dropwise 1.37 g. (0.024 mole) of methylisocyanate with stirring, and stirring was continued for 30 minutes. The solid which crystallized in the flask was recrystallized using 95% ethanol to give 5.0 g. (76%) of product (m.p. 145°-147° C.).

Analysis: Calculated for $C_{12}H_{13}F_3N_2O_2$: C, 52.56; H, 4.78; N, 10.22. Found: C, 52.67; H, 4.78; N, 10.16.

EXAMPLE 5

N-Methyl 3-(2-trifluoromethylphenoxy)-1-azetidinecarboxamide

To a stirring solution of 3-(2-trifluoromethylphenoxy) azetidine (4.5 g., 0.02 mole) in 50 ml. of dry benzene was added slowly at room temperature 1.2 g. (0.02 mole) of methylisocyanate. After an additional 30 minutes a solid separated which was collected and recrystallized from benzene. The product (3.5 g., 68%) melted at 134°-136° C.

Analysis: Calculated for $C_{12}H_{13}F_3N_2O_2$: C, 52.56; H, 4.78; N, 10.22. Found: C, 52.28; H, 4.78; N, 10.07.

EXAMPLE 6

N-Methyl 3-(3-aminocarbonylphenoxy)-1-azetidinecarboxamide

To a stirring solution of 7.0 g. (0.036 mole) of 3-(3-azetidinyloxy)benzamide in 75 ml. of dry benzene was slowly added 2.0 g. (0.036 mole) of methylisocyanate. Stirring was continued at room temperature for one hour. The solid which separated was filtered and recrystallized from 60% ethanol. The product weighed 6.0 g. (67%) and melted at 238°-240° C.

Analysis: Calculated for $C_{12}H_{15}N_3O_3$: C, 57.82; H, 6.07; N, 16.86. Found: C, 57.74; H, 6.13; N, 16.74.

EXAMPLE 7

N-Methyl 3-(4-aminocarbonylphenoxy)-1-azetidinecarboxamide

To a stirring solution of 5.0 g. (0.026 mole) of 4-(3-azetidinyloxy)benzamide in 75 ml. of dry benzene was added dropwise 1.5 g. (0.026 mole) of methylisocyanate. Stirring was continued for 1.5 hours. The white solid which separated was filtered and recrystallized using 95% ethanol. The solid was triturated with acetonitrile (due to solvation effects of the ethanol). The product weighed 4.0 g. (58%) and melted at 208°-210° C.

Analysis: Calculated for $C_{12}H_{15}N_3O_3$: C, 57.82; H, 6.07; N, 16.86. Found: C, 57.68; H, 6.10; N, 16.66.

FORMULATION AND ADMINISTRATION

The pharmacologically active N-lower-alkyl-3-phenoxy-1-azetidine-carboxamides of this invention are effective in the treatment of both petit mal epilepsy and grand mal epilepsy. Effective quantities of these compounds may be administered to a living animal body orally as in capsules, tablets or elixirs. It is only necessary that the active ingredient constitute an effective amount, i.e., such that a suitable effective dosage will be obtained consistent with the dosage form employed. The exact individual dosage as well as daily dosages will, of course, be determined according to standard medical principles under the direction of a physician or veterinarian.

Based upon a comparison with known anticonvulsant compounds, daily dosages appear to preferably range from about 0.5 to 1.5 milligrams per kilogram of body weight in the treatment of petit mal epilepsy and about 25 to 35 milligrams per kilogram of body weight in the treatment of grand mal epilepsy. Very small quantities of the active materials of the present invention, even as low as 0.1 milligram, are effective when minor therapy is involved. Unit dosages are usually 5 milligrams or above and preferably 25, 50 or 100 milligrams per unit dose. The active ingredients of the invention may be combined with other pharmacologically active agents as previously indicated, or with buffers, antacids or the like, for administration and the proportion of the active agent in the composition may be varied widely.

CAPSULES

Capsules of 5 mg., 25 mg., and 50 mg. of active ingredient per capsule are prepared; with higher amounts of ingredient reduction may be made in the amount of lactose.

| Typical blend for encapsulation | Per Capsule, mg. |
| --- | --- |
| Active ingredient | 5.0 |
| Lactose | 296.7 |
| Starch | 129.0 |
| Magnesium stearate | 4.3 |
| Total | 435.0 mg. |

Uniformly blend the selected active ingredient with lactose, starch and magnesium stearate and encapsulate the blend.

Additional capsule formulations preferably contain a higher dose of active ingredient and are as follows:

| Ingredients | 100 mg. per Capsule | 250 mg. per Capsule | 500 mg. per Capsule |
| --- | --- | --- | --- |
| Active ingredient | 100.0 | 250.0 | 500.0 |
| Lactose | 231.5 | 126.5 | 31.1 |
| Starch | 99.2 | 54.2 | 13.4 |
| Magnesium stearate | 4.3 | 4.3 | 5.5 |
| Total, mg. | 435.0 | 435.0 | 550.0 |

TABLETS

A typical formulation for a tablet containing 5.0 mg. of active ingredient per tablet follows. The formulation may be used for other strengths of active ingredient by adjustment of weight of dicalcium phosphate.

| Ingredients | Per Tablet, mg. |
|---|---|
| (1) Active ingredient | 5.0 |
| (2) Corn Starch | 13.6 |
| (3) Corn Starch (paste) | 3.4 |
| (4) Lactose | 79.2 |
| (5) Dicalcium phosphate | 68.0 |
| (6) Calcium Stearate | 0.9 |
| Total | 170.1 mg. |

Uniformly blend 1, 2, 4 and 5. Prepare 3 as a 10 percent paste in water. Granulate the blend with the starch paste and pass the wet mass through a number eight mesh screen. The wet granulation is dried and passed through a number twelve mesh screen. The dried granules are blended with calcium stearate and compressed.

Additional tablet formulations preferably contain a higher dosage of the active ingredient and are as follows.

| 50 mg. Tablet | |
|---|---|
| Ingredients | Per Tablet, mg. |
| Active ingredient | 50.0 |
| Lactose | 90.0 |
| Milo starch | 20.0 |
| Corn starch | 38.0 |
| Calcium stearate | 2.0 |
| Total | 200.0 |

Uniformly blend the active ingredient, lactose, milo starch and corn starch. The blend is granulated, using water as a granulating medium. The wet granules are passed through an eight mesh screen and dried at 140 to 160 degrees Fahrenheit overnight. The dried granules are passed through a number ten mesh screen and blended with the proper amount of calcium stearate and this blend is then converted into tablets on a suitable tablet press.

What is claimed:

1. A compound selected from N-lower-alkyl 3-phenoxy-1-azetidinecarboxamides having the formula:

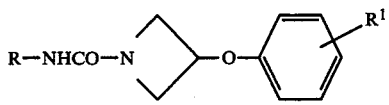

wherein R is lower alkyl and $R^1$ is hydrogen, aminocarbonyl or trifluoromethyl.

2. A compound of claim 1 which is N-methyl-3-phenoxy-1-azetidinecarboxamide.

3. A compound of claim 1 which is N-methyl-3-(4-trifluoromethylphenoxy)-1-azetidinecarboxamide.

4. A compound of claim 1 which is N-methyl-3-(3-trifluoromethylphenoxy)-1-azetidinecarboxamide.

5. A compound of claim 1 which is N-methyl-3-(2-trifluoromethylphenoxy)-1-azetidinecarboxamide.

6. A compound of claim 1 wherein $R^1$ is aminocarbonyl.

7. A compound of claim 1 wherein $R^1$ is trifluoromethyl.

8. A process which comprises orally administering to a living animal body for its anit-convulsant effect an effective amount of a compound selected from the group consisting of N-lower-alkyl 3-phenoxy-1-azetidinecarboxamides of the formula:

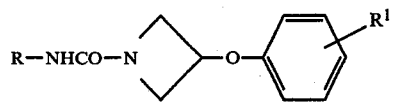

wherein R is lower alkyl and $R^1$ is hydrogen, aminocarbonyl or trifluoromethyl in admixture with a pharmaceutically acceptable carrier.

9. The process as defined in claim 8 wherein the compound is N-methyl-3-phenoxy-1-azetidinecarboxamide.

10. The process as defined in claim 8 wherein the compound is N-methyl-3-(4-trifluoromethylphenoxy)-1-azetidinecarboxamide.

11. The process as defined in claim 8 wherein the compound is N-methyl-3-(3-trifluoromethylphenoxy)-1-azetidinecarboxamide.

12. The process as defined in claim 8 wherein the compound is N-methyl-3-(2-trifluoromethylphenoxy)-1-azetidinecarboxamide.

13. The process as defined in claim 8 wherein $R^1$ is trifluoromethyl.

14. The process as defined in claim 8 wherein $R^1$ is aminocarbonyl.

15. An anti-convulsant composition comprising (a) an effective amount of a compound of the formula:

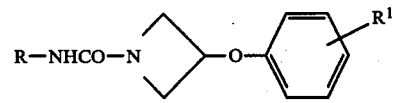

wherein R is lower alkyl, and $R^1$ is hydrogen, aminocarbonyl, or trifluoromethyl, and (b) a pharmaceutically acceptable carrier therefor.

16. A composition according to claim 15 wherein the compound is N-methyl-3-phenoxy-1-azetidinecarboxamide.

17. A composition according to claim 15 wherein the compound is N-methyl-3-(4-trifluoromethylphenoxy)-1-azetidinecarboxamide.

18. A composition according to claim 15 wherein the compound is N-methyl-3(3-trifluoromethylphenoxy)-1-azetidinecarboxamide.

19. A composition according to claim 15 wherein the compound is N-methyl-3-(2-trifluoromethylphenoxy)-1-azetidinecarboxamide.

20. A composition according to claim 15 wherein $R^1$ is trifluoromethyl.

21. A composition according to claim 15 wherein $R^1$ is aminocarbonyl.

* * * * *